United States Patent [19]
Leonhardt et al.

[11] Patent Number: 5,957,949
[45] Date of Patent: Sep. 28, 1999

[54] PERCUTANEOUS PLACEMENT VALVE STENT

[75] Inventors: Howard J. Leonhardt; Trevor Greenan, both of Sunrise, Fla.

[73] Assignee: World Medical Manufacturing Corp., Sunrise, Fla.

[21] Appl. No.: 08/848,892

[22] Filed: May 1, 1997

[51] Int. Cl.$^6$ .................................................. A61M 29/00
[52] U.S. Cl. .......................... 606/194; 606/108; 606/195; 606/198; 623/1; 623/2; 623/12
[58] Field of Search ..................... 606/108, 194, 606/195, 198, 200; 623/1, 2, 12

[56] References Cited

U.S. PATENT DOCUMENTS

| | | | |
|---|---|---|---|
| 4,733,665 | 3/1988 | Palmaz | 606/108 |
| 5,163,953 | 11/1992 | Vince | 623/2 |
| 5,411,552 | 5/1995 | Andersen et al. | 623/2 |
| 5,591,195 | 1/1997 | Taheri et al. | 606/194 |
| 5,665,103 | 9/1997 | Lafontaine et al. | 606/194 |
| 5,667,523 | 9/1997 | Bynon et al. | 606/194 |

Primary Examiner—Michael Powell Buiz
Assistant Examiner—Daphna Shai
Attorney, Agent, or Firm—Paul F. Bawel

[57] ABSTRACT

An artificial valve stent for maintaining patent one way flow within a biological passage is disclosed. The artificial valve includes a tubular graft having radially compressible annular spring portions for biasing proximal and distal ends of the graft into conforming fixed engagement with the interior surface of a generally tubular passage. Also disclosed is a deployment catheter including an inner catheter having a nitinol core wire, a controllable tip balloon at its the distal end for dilation and occlusion of the passage, and a controllable graft balloon in the vicinity of and proximal to the tip balloon for fixedly seating the spring portions in conformance with the interior surface of the passage. A spool apparatus for adjusting or removing an improperly placed or functioning artificial valve, and a microembolic filter tube are usable with the deployment catheter. The artificial valve may be completely sealed to the living tissue by light activated biocompatible tissue adhesive between the outside of the tubular graft and the living tissue. A method of implanting the artificial valve is also disclosed.

17 Claims, 8 Drawing Sheets

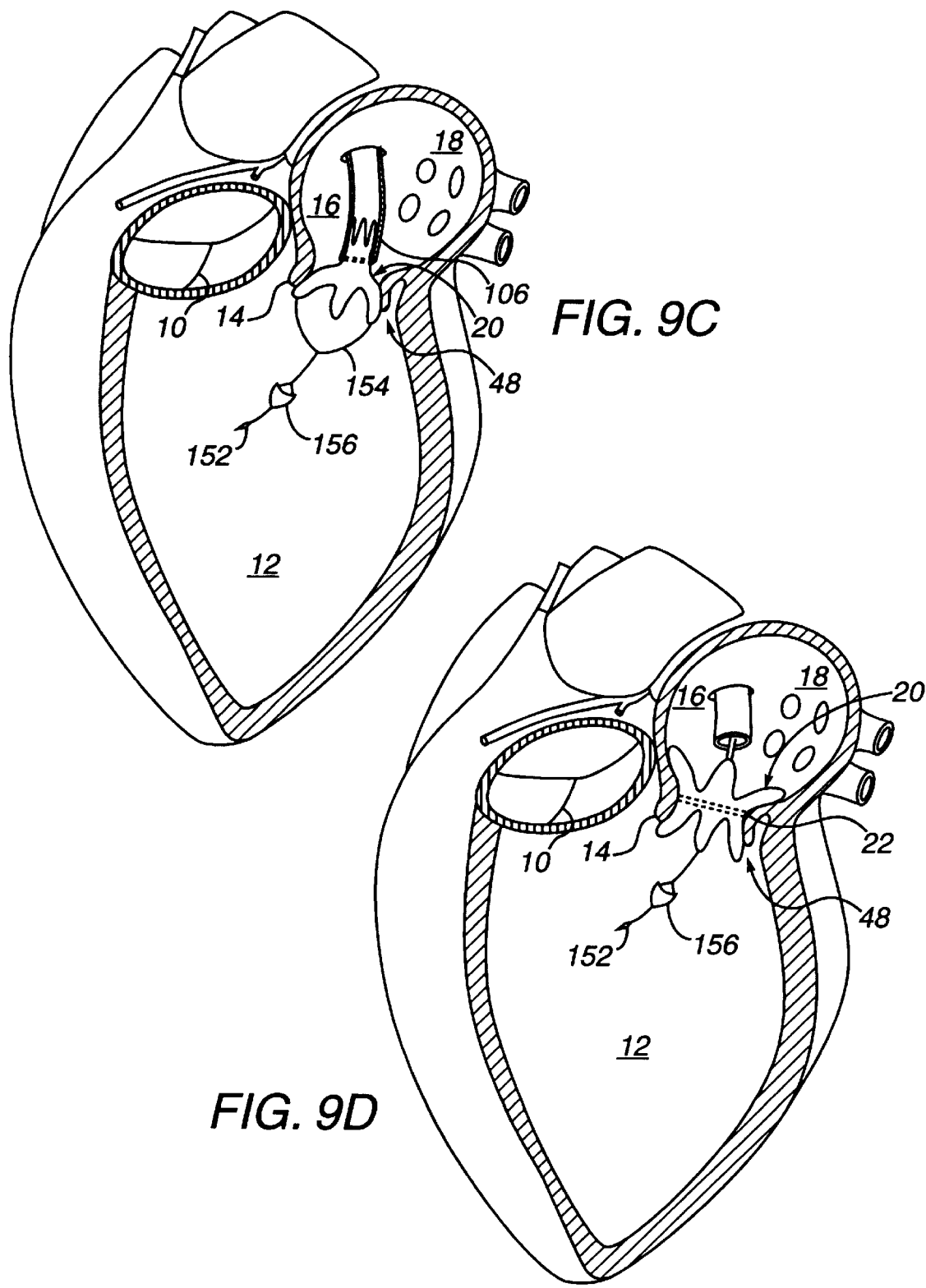

PERCUTANEOUS PLACEMENT VALVE STENT

FIELD OF THE INVENTION

This invention relates to artificial valves, specifically those placed percutaneously by a catheter. The artificial valve disclosed may replace existing valves such as are in the heart or esophagus, or may be placed where fluid flow needs to be maintained in one direction only.

BACKGROUND OF THE INVENTION

The disclosed invention involves a percutaneously placed artificial valve to maintain bodily fluid flow in a single direction. It opens and closes with pressure and/or flow changes. The invention may be placed anywhere flow control is desired. To facilitate the discussion of the disclosure, use as a heart valve will be addressed. Heart valves are selected because they provide the highest risk to the patient during placement, and in terms of lowering the risk while providing a superior device the advantages of this valve are clearly presented. It is understood that the device and method disclosed are available to all valvular needs.

Cardiac valve prostheses are well known in the treatment of heart disease. The normal method of implantation requires major surgery during which the patient is placed on a heart-lung machine and the patient's heart is stopped. Once the surgery is complete, the patient can expect an extended hospital stay and several more weeks of recuperation. A mortality rate of five percent (5%) is common. For some patients, surgery is not an option because age or some other physical problem prevents them from being able candidates for surgery due to the inherent dangers and the likelihood of death therefrom.

The valve devices themselves fall into two categories, either biological or mechanical. Biological heart valves are either homograft (a recent human harvest), allograft (a stored human harvest) or xenograft (a stored animal harvest). Homografts are rare because of the well known problems of locating and matching human donors in both tissue type and size. Allografts are also in short supply because of lack of donors. Xenografts are common and well accepted, usually from bovine or porcine donors, and many times the actual heart valve from the animal is used. These devices may be accompanied by immunological rejection from the human body when sutured directly to human tissue and require the patient to take anti-rejection drugs which suppress the immune system. Generally, the valves are treated to reduce the antigenicity of the valve tissue, but the effect is to limit the life of the valve to about ten years.

Mechanical valves may be either a ball valve or a leaflet valve having one to three leaflets. One leaflet valve, U.S. Pat. No. 5,469,868, closely resembles a biological valve having three synthetic resin leaflets. Mechanical valves are susceptible to clot formation and require the patient to maintain a strict regiment of anticoagulant drugs which carry their own associated risks. Furthermore, some mechanical valves are prone to wear leading to failure, and some materials for mechanical valves are subject to supply problems.

The majority of these artificial valves require surgery and the stopping of the heart as discussed above. During implantation, the valve must be sewn in place either at the natural valve location or at a location adjacent to the natural valve. Even new laproscopic techniques, while substantially less invasive, require general anesthesia and a heart-lung machine. There are artificial valves which claim to have overcome the problems of implantation of the commonly used valves.

Three artificial valves which claim the ability to be placed percutaneously comprise the nearest prior art. They are the Tietelbaum valve, U.S. Pat. No. 5,332,402; the Pavcnik valve, U.S. Pat. No. 5,397,351; and the Andersen valve, U.S. Pat. No. 5,411,552. Each of these devices allow placement by minimally invasive techniques. However, each of the devices have disadvantages upon which the disclosed invention greatly improves.

The Teitelbaum valve uses nitenol to form each of the two major elements of the valve. It is a mechanical valve, and as such is prone to embolism formation. The two types of stoppers, a ball and seat and an umbrella and seat, each reduce the passageway diameter through the valve thereby reducing the efficiency of blood flow through the valve, and the efficiency of the cardiovascular system itself. Being of two separate components, the movement adds extra complexity leading to wear and improper seating. The abundance of metal in direct contact with the tissue requires a hydrophilic coating which may or may not prevent stenosis in the valve passageway. This valve may only be placed in the natural valve's position and not elsewhere in the vascular system. Also, the nitenol design proposed requires cooling to make it sufficiently compliant to fit within the placement catheter. Cooled nitenol does not exhibit sufficient force upon warming and reformation of its intended shape to maintain a seal between the stent and the tissue. Lastly, both elements must be inserted independently of the other requiring multiple delivery catheters.

The Pavcnik valve is also a mechanical valve of ball and seat design. It utilizes a Gienturco stent (U.S. Pat. No. 4,580,586) capped by a cage to comprise a complex restraining element for the ball which is difficult to manufacture. The restraining element must be attached to the seat by a connecting member to maintain the proper distance between the two. The ball is made of latex which can cause a reaction with living tissue. The seat is comprised of two rings, one smaller than the other, displaced from each other by nylon mesh. Both the seat and the restraining element are stainless steel which must be fairly stiff and non-compliant to maintain sufficient outward bias thereby severely restricting the natural movement of the cardiovascular system at the point of implantation. There are multiple joints which must be soldered together increasing the potential for joint failure and breakage. This device requires hooks to maintain patency in the tissue, requiring surgery to remove once deployed. Repositioning is not possible because of the hooks. The balloon must be inserted in a deflated state and filled after placement within the cage and seat. The filling liquid is a silicone rubber which can have detrimental effects on the health of the patient if leaked into the blood stream. In whole, this is a complex design which is highly susceptible to thrombi emboli and improper function over time.

The Andersen valve comprises a stainless steel stent to secure a biological valve. The stent is formed of two or more wavy rings sutured to each other with the top loop requiring projecting apices to secure the commissural points of the valve. The valve claims reduced weight but looses this advantage by requiring multiple rings to attain patency against the tissue. The device requires a special trisection balloon with three or more projecting beads to secure the valve within the deployment catheter during placement, and the stent does not exert sufficient force against the tissue to remain in place without a balloon expanding the stent tightly into the tissue wall. The stiffness of stainless steel does not comply with the natural movement of the cardiovascular system which may lead to stenosis at the implantation point. Furthermore, the suture points connecting the multiple rings are subject to movement and wear against each other and therefore the sutures or the rings may break at the connecting points.

One drawback of all three of these valves is that none of the devices may be removed or repositioned once they are expressed from their placement catheter. Any misplacement or failure requires major open heart surgery equal to or greater than that now required by standard procedures. Many patients which receive the valve percutaneously because of their intolerance to surgery would face a very uncertain outcome from misplacement or failure. Also, none of these devices seal to the living tissue at the outside wall of the prosthesis. Leaks, and therefore emboli, are likely results after implantation.

The need remains for an artificial heart valve which is placed percutaneously through a single minimally invasive entry point; which will seal at the outside wall of the valve with the living tissue of the patient; which may be placed percutaneously at any point as well as directly over an existing vascular or cardiac valve; which will not cause thrombi emboli to form at the valve thereby removing the need for anticoagulant drugs; which will comply with the natural motion of the tissue to which it is attached; which will not cause stenosis; which does not require general anesthesia or stopping the heart or using a heart-lung machine during placement; which will reduce the recuperation time after placement both in and out of the hospital; and which may be repositioned or removed after placement in the event of such a need.

SUMMARY OF THE INVENTION

A percutaneously implanted artificial valve maintains patent one way flow within a biological passage and includes a tubular graft having radially compressible annular spring portions for biasing proximal and distal ends of the graft into conforming fixed engagement with the interior surface of a generally tubular passage. The graft material is attached to and encloses the annular spring preventing contact between the spring and living tissue. A valve is sealingly and permanently attached to the internal tubular portion of the valve graft. The artificial valve graft may be completely sealed to the living tissue by light activated biocompatible tissue adhesive between the outside of the tubular graft and the living tissue.

A BRIEF DESCRIPTION OF THE DRAWINGS

FIGS. 9a–9d are a series of elevational views depicting a method of deploying the valve stent in the mitral valve position.

DETAILED DESCRIPTION OF THE PREFERRED EMBODIMENT

Figure 3:
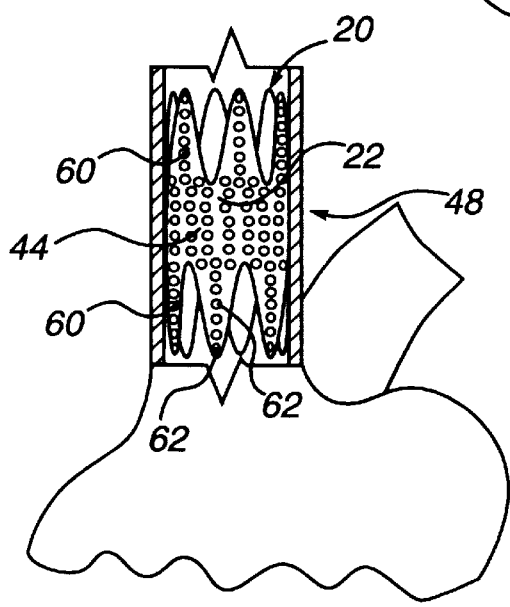
FIG. 3 is an elevational view of the valve stent fully deployed within the aorta above the aortic valve.
Figure 4:
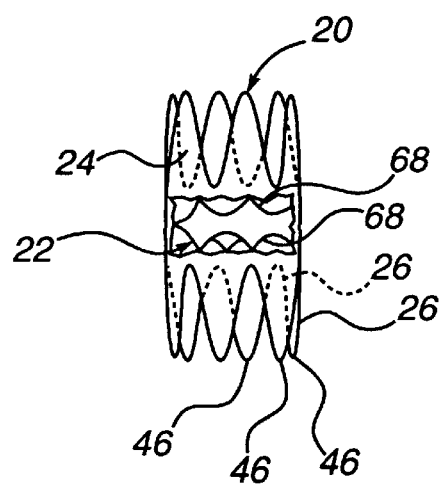
FIG. 4 is a sectional view showing the biological valve within the stent.

FIG. 4 shows the preferred embodiment of valve stent 20, comprised of three elements. The three elements are stent 26, biological valve 22, and graft material 24. FIGS. 3, 5, 7A, and 7B illustrate accessories and options associated which the preferred embodiment, including the deployment catheter 100, the bioadhesive material 56 or bioadhesive packets 62, the spool apparatus 170, and the microembolic filter tube 182.

For purposes of the disclosed invention and its apparatuses, the distal end is the end first inserted into the patient and the proximal end is the end last inserted into the patient.

Figure 1:
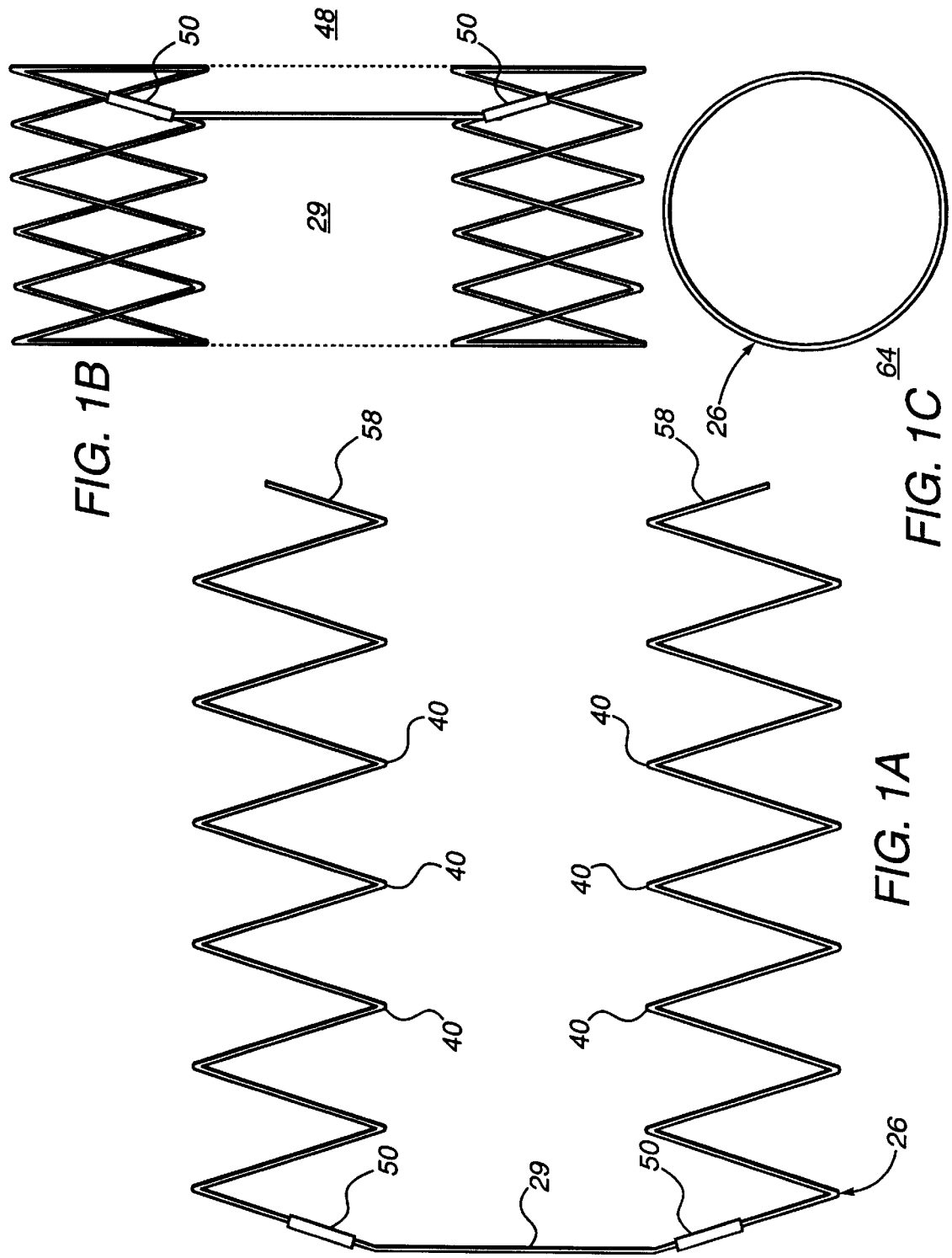
FIG. 1a is an perspective view of the super elastic spring stent in its permanent shape prior to attaching the ends to form the cylindrical walls.
FIG. 1b is an perspective view of the super elastic spring stent in its permanent shape after attaching the ends to form the cylindrical walls.
FIG. 1c is a top view of the super elastic spring stent in its permanent shape after attaching the ends to form the cylindrical walls.

Stent 26 is shown in FIGS. 1a–1c. FIG. 1a shows stent 26 formed of a single piece of super elastic wire, preferably nitenol wire, with two crimping tubes 50. The crimping tubes 50 is preferable of the same material as the wire to avoid problems which occur when dissimilar materials are in electrical contact with each other, however other materials known in the art may be used. Stent 26 is in its permanent shape, although it has not yet had its two ends attached to itself to form cylindrical wall 64 (FIG. 1C) which will support the other elements of valve stent 20. The top and bottom portions are substantially symmetrical to each other having a zig-zag 40 or wavy form. The preferred embodiment has six (6) zig-zags 40 which optimizes its compressed diameter and outward force, but more or less may be used.

At each end of stent 26 is a short extension 58 beginning another zig or wave. Short extension 58 is to close and attach the end to the first zig or wave closest to connecting bar 29. Short extension 58 and the portion of stent 26 to which crimping tubes 50 enclose are substantially parallel to each other to facilitate their connection.

The connection is achieved through a crimping tube 50 as shown in FIG. 1b, or by permanent adhesives or welding which are not shown. As is seen in FIG. 1c, the crimped connection is made such that the short extension 58 falls substantially within the area of cylinder wall 64 formed when the connection is complete.

FIG. 1b shows stent 26 in its completed form with crimping tubes 50 crimped. This form creates an imaginary cylinder 48 which will exert an approximate outward force of 350 grams or more at each end. An outward force of 350 grams at the mitral valve position is sufficient to secure the valve stent, however stent 26 may be manufactured with more or less outward force to accommodate other placement positions. The super elasticity of the material allows it to deform to forces exerted on it only at those points experiencing the deforming force. All other points will seek their permanent shape. This allows stent 26 to conform to and seal against the dramatically different structures occurring within vessel walls and valve locations with one basic stent shape.

Stent 26 is a continuous super elastic nitenol wire having a distal end and a proximal end. Both the distal end and the proximal end are substantially identical, both forming a cylinder wall 64 of six zig-zags 40 or waves. Each end is pre-sized in diameter to be approximately thirty percent (30%) larger in diameter than the largest diameter of the tissue against which the valve stent 20 (FIG. 3) will seal. The overall length of stent 26 is also pre-sized to be sufficient to maintain patency against fluid flow in the vessel or natural valve position, as well as completely support the biological valve (or mechanical or synthetic valve) without causing valve 22 to suffer prolapse or insufficiency.

The nitinol wire used to form stent 26 is a super elastic straight annealed material formed substantially of titanium and nickel. It may be coated with a biocompatible material, such as titanium oxide, which will reduce the tissue's reaction to the nickel and improve radiopacity. A layer of PTFE may also cover stent 26 to reduce the risk of blood clotting and corrosion. Furthermore, stent 26 may be treated with iridium 192 or other low dose Beta radiation emitting material to reduce post-surgical cell proliferation in the vessel or valve position. Valve stent 20 may have radio opaque markers in predetermined positions to aid in deployment and placement.

Each zig-zag 40 or wave is equidistant from the next in its set and all are of the same height. The peaks and valleys forming the waves are all of a predetermined radius to maximize the spring bias and prevent sharp transitions which create weak points in stent 26. Once crimped, stent 26 forms two cylinders, one at each end of stent 26. Each cylinder is substantially directly above or below the other cylinder.

The cylinders are spaced a predetermined distance from each other by a connecting bar 29 which is the central part of the continuous wire from which stent 26 is formed. Connecting bar 29 is also biased outward to conform to the living tissue so as to minimally disrupt blood or other fluid flow, thereby minimizing the possibility of clotting. It is also covered by and sutured to graft material 24 (FIG. 4). Connecting bar 29 provides torsional stability for valve stent 20.

Figure 2:
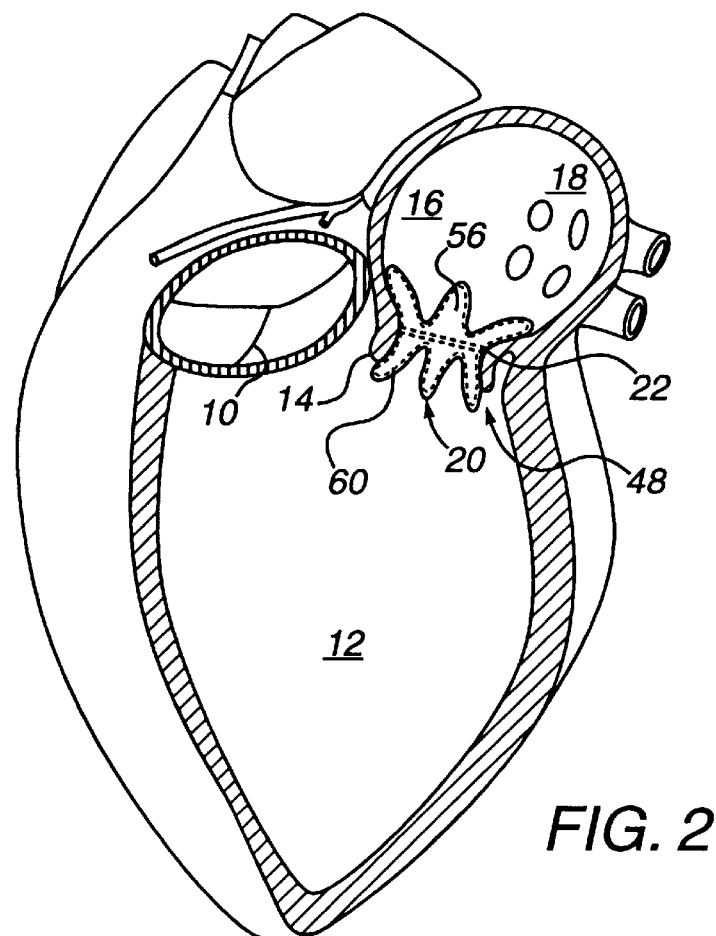
FIG. 2 is an elevational view of the valve stent fully deployed within the mitral valve.

FIG. 2 presents a complete pre-sized valve stent 20 fully deployed in the location of mitral valve 14. Also refer to FIG. 4 to identify elements in the following discussion. Mitral valve 14 has been prepared for deployment by valvuloplasty to remove plaque and fistulas if necessary. Valve stent 20 comprises a malleable graft material 24 enclosing deformable self-expanding stent 26 to which a biological valve 22 is attached. Stent 26 biases the proximal and distal ends of valve stent 20 into conforming and sealingly fixed engagement with the tissue of mitral valve 14. The deployed valve stent 20 creates a patent one way fluid passageway.

Graft material 24 is a thin-walled biocompatible, flexible and expandable, low-porosity woven fabric, such as polyester or PTFE. It is capable of substantially conforming to the surface of the living tissue to which stent 26 coerces it. Graft material 24, through its low porosity, creates the one-way fluid passage when sutured to the cylindrical form of stent 26. The middle portion of graft material 24 is tapered to a smaller cross-sectional area than its ends to prevent bunching of the material once placed within the patient.

Stent 26 is sutured within graft material 24 using polyester suture 60. Prior to sewing, graft material 24 is arranged to surround stent 26 and is heat pressed to conform to the distal and proximal cylindrical ends of stent 26 using an arcuate press surface (not shown). The arcuate press surface is heated to 150 degrees Fahrenheit and corresponds in curvature to the distal and proximal ends. A preferred stitching pattern involves two generally parallel stitches, one on each side of the wire, and a cross-over stitch (not shown) around the wire for pulling the stitches together. This achieves tight attachment of graft material 24 to stent 26 thereby preventing substantially all contact between stent 26 and living tissue. The stitching also will be reliable over the life of the patient.

Where other vessels or passages leave the vessel receiving valve stent 20 at a placement site, or when valve stent 20 must flair at one or both ends as is shown in FIG. 2, graft material 24 may be cut out between the plurality of distensible fingers 46 formed by zig-zags 40 of stent 26. Distensible fingers 46 form a conical tip when compressed together which facilitates loading valve stent 20 in the deployment catheter (FIG. 5) prior to the procedure and if retrieval after deployment is necessary. Valve stent 20 may be placed such that other vessels are not blocked by placing distensible fingers 46 on either side of the vessel junction. Stent 26 is pre-sized to open beyond the width of the natural valve mouth and will flair sufficiently to conform and seal to the tissue.

Biological valve 22 is preferably a porcine valve treated and prepared for use in a human. It has two or more commissural points 68 as is seen in FIG. 4. Biological valve 22 is attached to stent 26, to graft material 24, or both with sutures 60 or biocompatible adhesive or a combination of the two. Biological valve 22 is pre-sized to fit within the internal diameter of cylinder 48 formed by stent 26 attached to graft material 24. Attachment is along biological valve's 22 commissural points 68 and around its base. Whereas a biological valve is preferred, a mechanical valve or a synthetic leaflet valve may also be employed.

Figure 5:
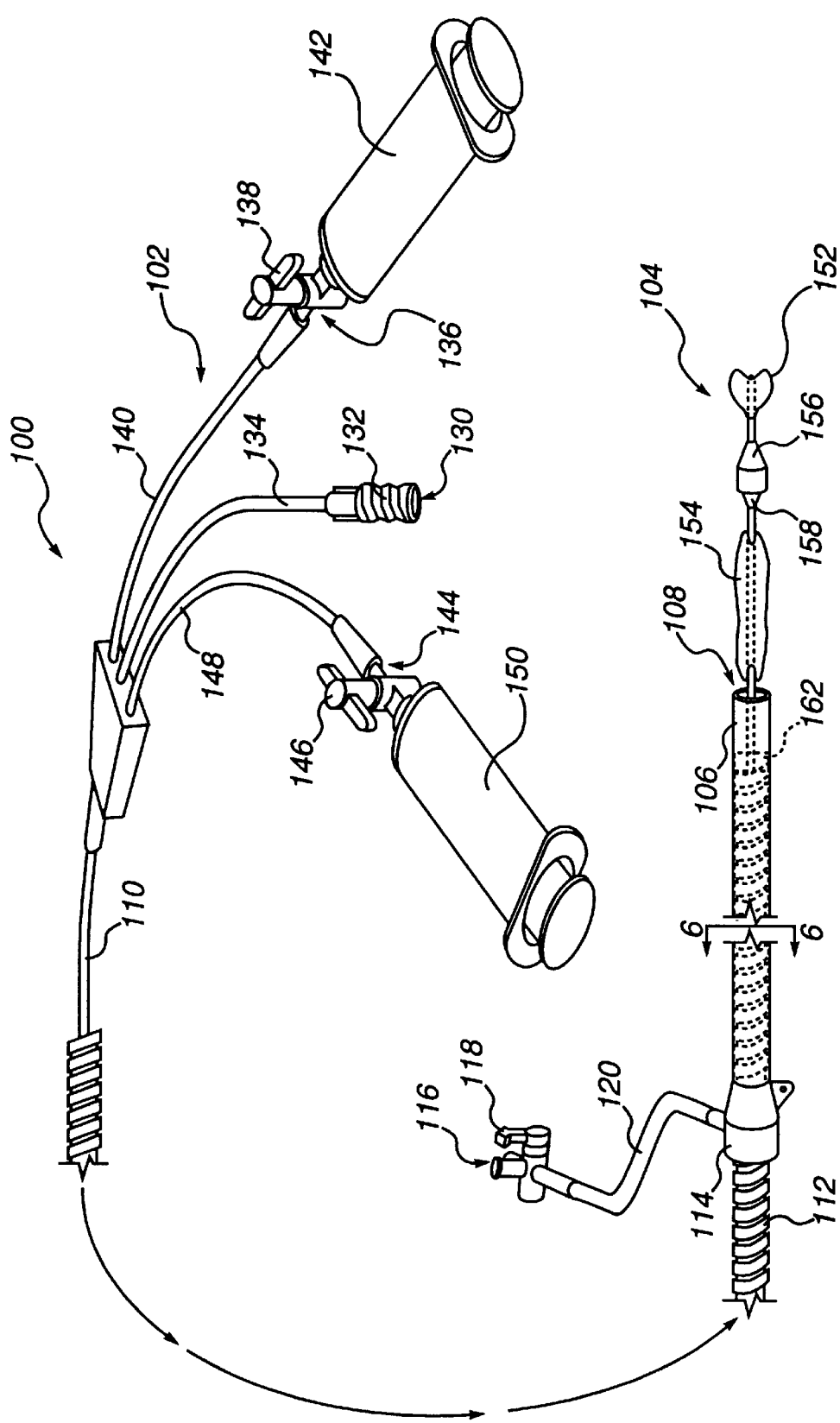
FIG. 5 is a perspective view of the deployment means of the present invention.
Figure 6:
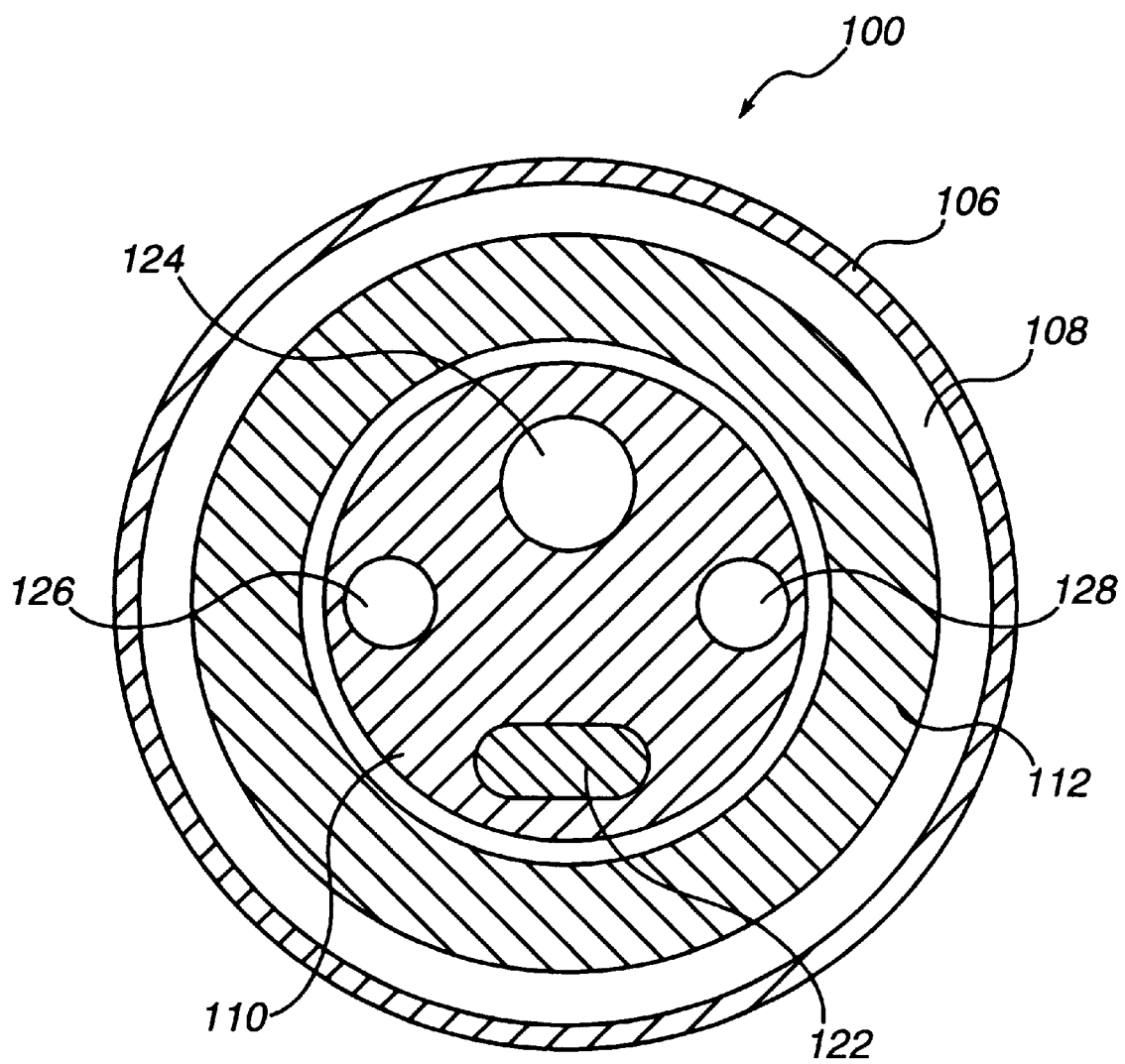
FIG. 6 is a sectional view thereof taken generally along the line 6—6 in FIG. 5.

A preferred deployment catheter 100 is illustrated in FIGS. 5 and 6. Deployment catheter 100 is generally long and tubular permitting percutaneous delivery of valve stent 20 to the placement site. Deployment catheter 100 has a proximal end remaining outside of the patient and a distal end which is inserted into the patient. The proximal end allows access to a plurality of lumens, syringes, filter tube 182, spool apparatus 170, and other apparatus as necessary for implantation of the disclosed invention. Outer sheath 106 has an axially extending sheath passage 108 and receives an elongated compression spring push rod 112 within sheath passage 108. A push rod 112 also has a passage extending through its longitudinal axis created by the spring coils. Inner catheter 110 is slidably mounted within push rod 112 passage.

Outer sheath 106 is made of a low friction and flexible material, preferably PTFE. Other suitable materials such as polyurethane, silicone, polyethylene may be used instead of PTFE. The material is preferably clear to allow inspection of valve stent 20 and deployment catheter 100 prior to use.

The size of outer sheath 106 depends on the size of valve stent 20 to be implanted. Common sizes range from 12 FR to 20 FR. Collapsing distensible fingers 46 of valve stent 20 together forms a conical tip which allows for easy loading by sliding outer sheath 106 over the tip and on until valve stent 20 resides within outer sheath 106 and beyond by approximately five millimeters. The conical tips allow a reduction in the profile of valve stent 20 of 2 FR, which allows a smaller diameter outer sheath 106 to be used. This results in a smaller entry incision and less trauma to the patient's access passageway.

Outer sheath 106 has a side port means 116 near its proximal end. Side port means 116 provides access for transporting fluid, such as heparin or contrast dye, through outer sheath 106 passage and into the patient. Side port means 116 includes a manually operated valve in fluid communication with outer sheath 106 passage through a flexible tube adapted to receive suitable fluid injection means (not shown). Proximal to side port means 116, outer sheath 106 has at least one latex-lined homeostasis valve (not shown) for forming a fluid seal around push rod 112 to prevent blood or other fluid from leaking out of the delivery catheter at the proximal end.

Biological valve 22 should be in an open position when valve stent 20 is loaded into outer sheath 106. This reduces overall profile and stress on biological valve 22 and its attachment to stent 26 and cover material. An open valve 22 also allows inner catheter 110 to pass through valve 22 prior to and during deployment with negligible chance of damage to the valve 22. Valve stent 20 is loaded either end first into outer sheath 106, the correct choice depending upon the access path taken and the fluid flow direction at the placement site. After placement, biological valve 22 should open in the direction of blood flow.

Inner catheter 110 is longer than either outer sheath 106 or push rod 112 permitting it to extend beyond outer sheath 106 and push rod 112 at both ends. Inner catheter 110 may be made of 8 FR catheter tubing. As is seen in FIG. 6, inner catheter 110 comprises an embedded, kink resistant nitinol core wire 122, a first inner track 124, a second inner track 126, and a third inner track 128, all extending lengthwise thereof. Referring to FIG. 5, a first end port means 130 for transporting fluid to first inner track 124 includes a threaded adapter 132 for mating with suitable fluid injection means (not shown) and communicating with a proximal end of first inner track 124 through a flexible tube. A second end port means 136 for transporting fluid to second inner track 126 includes a manually operable valve communicating with the proximal end of second inner track 126 through a flexible tube and adapted to receive a suitable fluid injection means. Similarly, a third end port means for transporting fluid to third inner track 128 includes a manually operable valve communicating with a proximal end of third inner track 128 through a flexible tube and adapted to receive a suitable fluid injection means.

A preferred option of core wire 122 is a gradual tapering from a diameter of approximately 0.031 inches at its proximal end to a diameter of approximately 0.020 inches at its distal end, with the distal tip of core wire 122 being rounded and smooth. This feature provides that the proximal end of inner catheter 110 is strong and the distal end of inner catheter 110 is less likely to puncture or rupture the access passage yet will not deflect significantly under the force of blood flow. Additional to being kink resistant and strong, core wire 122 displays superior torsional rigidity translating into substantial rotational equivalence along the entire length of core wire 122 when turning inner catheter 110 in either direction at the proximal end.

Second inner track 126 and third inner track 128 communicate with balloons at the distal end of inner catheter 110. Second inner track 126 allows filling and emptying tip balloon 152 and third inner track 128 allows filling and emptying expansion balloon 154. Expansion balloon 154 is larger in diameter and shaped according to the placement site Tip balloon 152 is essentially round and of necessary diameter to block blood flow to the placement site if needed. Balloons are preferably polyurethane and act in a calibrated pressure compliant manner such that injecting a known amount of fill fluid into balloons relates to a known expansion in the diameter of balloons. Also, withdrawing a known amount of fill fluid from balloons relates to a known contraction in the diameter of balloons. Fill fluid is preferable filtered carbon dioxide because of it radiopacity. Fill fluid is injected into second inner track 126 and third inner track 128 by separate fluid injection means, respectively. Fluid injection means may comprise a transparent volume-marked syringe with slidable plungers for observably controlling the plenum volume of the syringe filling or emptying a balloon.

Figure 8:
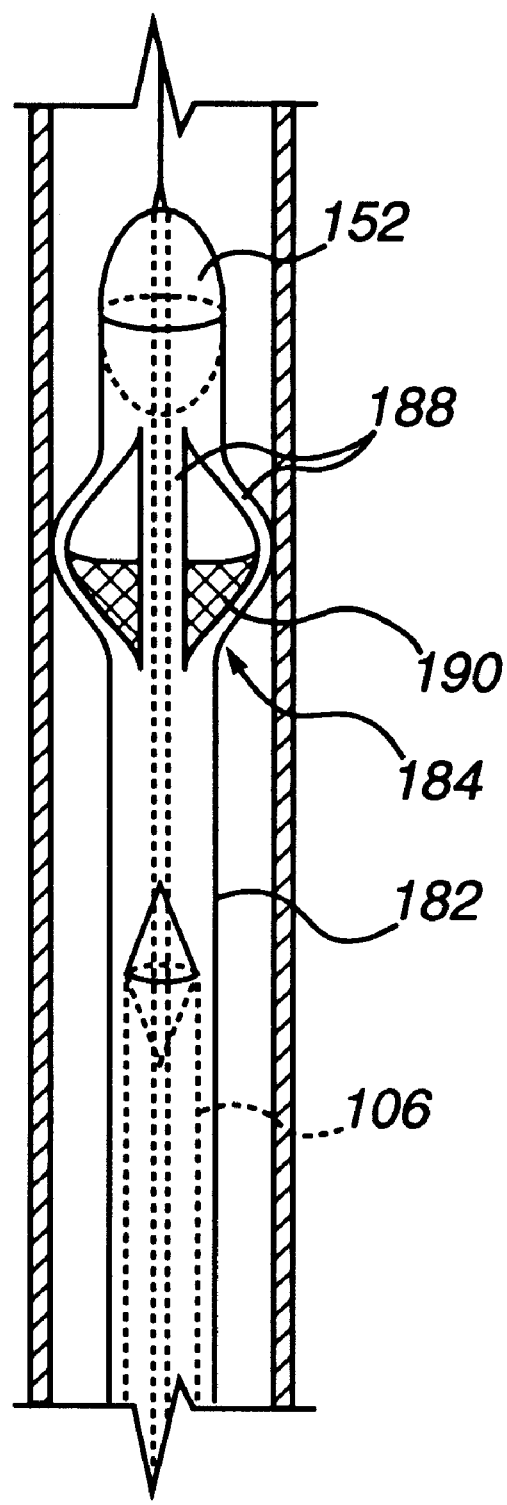
FIG. 8 is an elevational view showing a micro-embolic filter tube of the present condition in its deployed position.

Tapered head 156 resides between tip balloon 152 and expansion balloon 154. It allows a calm and smooth atraumatic transition from the profile of inner catheter 110 to the profile of outer sheath 106 or to the profile of microembolic filter tube 182 (FIG. 8). Tapered head 156 preferably defines a first annular abutment lip 158 arranged to engage the distal end of outer sheath 106 which prevents tapered head 156 from entering outer sheath 106 passage. Tapered head 156 may contain a second abutment lip (not shown) of slightly larger diameter than first abutment lip 158 or a flair from a smaller to a larger diameter beginning at the first abutment lip 158 for preventing the advancement of the distal end of microembolic filter tube 182 when it is being employed.

Push rod 112 is a metallic compression spring having a combination of flexibility and axial compression strength to enable it to follow a tortuous path without loosing its ability to act as a push rod for exerting force against valve stent 20 during deployment. Push rod 112 is smaller in diameter than outer sheath 106 such that both are independently slidable relative to the other. Push rod 112 has an internal path larger in diameter than inner catheter 110 such that both are independently slidable relative to the other. The distal end of push rod 112 defines a plunging seal 162 for stopping fluid flow into the deployment catheter 100 proximal to plunging seal 162. If spool apparatus 170 (FIG. 7a) is employed, either plunging seal 162 must be left out, or suture loops 174 must pass through the opening inner catheter 110 passes through, or one of the lumens or an extra lumen provides passage for suture loops 174. Push rod 112 may also include damping means (not shown) near its distal end, such as a thin heat-shrunken polyolifin or polyimid coating, which dampens undesirable recoil of push rod 112.

Valve stent 20 has several preferred options. One is light activated bioadhesive material 56 on the outside of graft material 24 shown in FIG. 2. Bioadhesive material 56 remains inert and will not bind until it is exposed to light waves of a specific frequency. Bioadhesive 56 will not react to sunlight or to standard bulbs found at home or in the operating room. Once deployment is complete and positioning and function verified, a light source (not shown) is inserted and energize. The source emits light of the proper frequency such that when bioadhesive 56 is exposed to the light it sets, binding valve stent 20 to the living tissue and sealing any small microleaks.

Another variation is bioadhesive material 56 which is contained in photosensitive polyurethane packets 62 as shown in FIG. 3, which degrade and release the adhesive when exposed to light of the proper frequency. Packets 62 are affixed to the outside of graft material 24 which will contact the living tissue. Again, once valve stent 20 is positioned and functioning, a light source is inserted and energized. Packets 62 then degrade and the bioadhesive 56 fills any microcracks in the seal and binds valve stent 20 in place. In this embodiment, bioadhesive 56 may or may not be photosensitive.

In either case, bioadhesive material 56 slowly degrades as it is replaced with living tissue which binds to valve stent 20 securing its location. Types of bioadhesive material 56 which may be used are cryroparticipate, fibrin glue or isobutyl 2 cyanoacrylate. There are also other bioadhesive materials 56 which will suffice such as are used and known in the dental and medical industry.

Figures 7A, 7B:
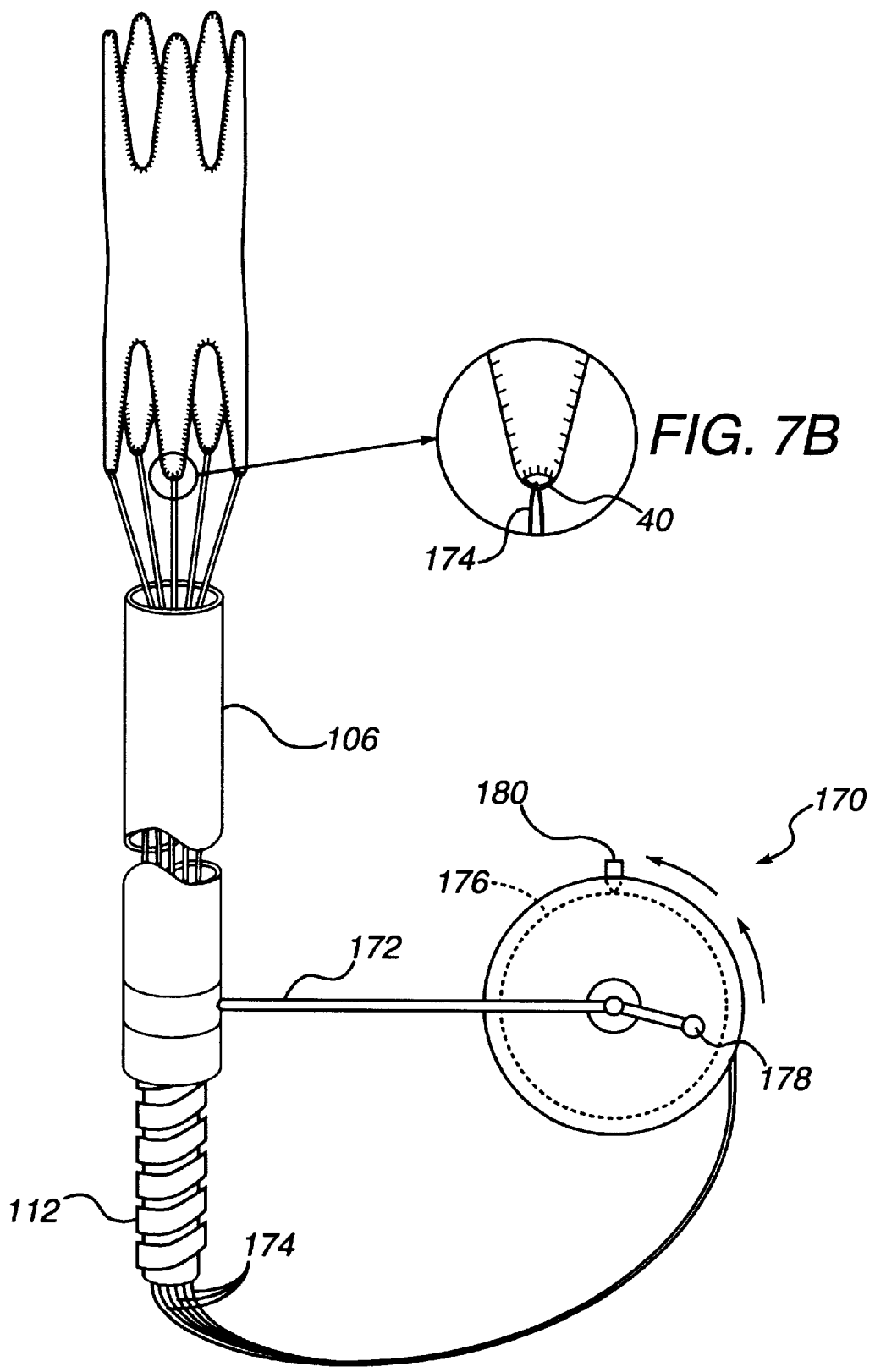
FIG. 7a is a perspective view showing a spool apparatus and retrieval means of the present invention.
FIG. 7b is an enlargement of the circled portion A in FIG. 7a showing the arrangement of a suture loop connecting the invention.

FIGS. 7a and 7b show another preferred option of the invention. A spool apparatus 170 may be provided as part of deployment catheter 100. Spool apparatus 170 allows valve stent 20 to be retrieved into outer sheath 106 if repositioning or removal is necessary. Referring to FIG. 7a, spool apparatus 170 is mounted adjacent the proximal end of outer sheath 106 by a mounting arm 172. Spool apparatus 170 includes a plurality of suture loops 174 wound around a spool cylinder 176 and arranged to extend through a central axial passage of push rod 112. FIG. 7b shows how suture loops 174 extend through the central axial passage, and through and around the peaks of stent 26 at its proximal end.

Included with spool apparatus 170 is a hand crank 178 and a releasable pawl (not shown) which work to rotate and fix spool cylinder 176 of spool apparatus 170. An optional blade 180 may be mounted on the body of the spool apparatus 170 for selectively and simultaneously cutting all suture loops 174 at one point to enable removal from valve stent 20 and deployment catheter 100.

A final preferred option of the invention is illustrated in FIG. 8. A micro-emboli filter tube 182 may be uses with deployment catheter 100 (FIG. 5) for trapping thrombus, plaque or other particles dislodged or occurring during either the valvuloplasty procedure or the deployment procedure. Filter tube 182 is sized to freely slide over outer sheath 106 and may include one or more pocket filters 184. All pocket filters 184 include a plurality of flexible spokes 188 defined by a series of axially extending slits substantially equispaced around the circumference of filter tube 182. Nylon mesh fabric 190 or the like is affixed along the bottom portion of spokes. When filter tube 182 is axially compressed by pushing its proximal end, spokes 188 of filter tube 182 flair and open pocket filters 184 which extend out and abut the vessel wall. The pockets thereby catch any passing thrombus. The distal end of filter tube 182 is held in place by either expanded tip balloon 152, expansion balloon 154 or tapered head 156. The proximal end of filter tube 182 is retracted to collapse flared spokes 188 and pocket filters 184, which in turn entraps any thrombus residing in pocket filters 184. Pocket filters 184 may be partially or fully collapsed during removal of deployment catheter 100. If necessary, filter tube 182 may be removed independently of deployment catheter 100.

FIGS. 9a–9d illustrate a method of surgically implanting valve stent 20. It is assumed that necessary mapping of the placement site and access path have been performed, and that an appropriately sized valve stent 20 has been selected and pre-loaded within the distal end of outer sheath 106 passage of appropriately sized deployment catheter 100. It is further assumed that certain equipment used for monitoring and visualization purposes is available for use by a surgeon skilled in the art. Such equipment includes a freely positional C-arm having high resolution fluoroscopy, high quality angiography, and digital subtraction angiography capabilities. Finally, it is assumed the patients heart has been slowed and blood pressure dropped if necessary.

Depending on the placement site, an access passage is chosen to minimize trauma to the passage and the patient. If the placement site is in the aorta or aortic valve 10, entry may be made through the largest femoral artery in the groin area and into the aorta. A high flow pig tail angiography catheter may be placed in the pathway and advanced into the thoracic aorta and an angiogram is performed. The angiography catheter may be left in place. A flexible guide wire with a tip balloon 152 is inserted through the same entry point and advanced to immediately above aortic valve 10 or into left ventricle 12. Deployment catheter 100, prefilled with heparinized solution through side port means 116, is then inserted through the entry point and into the patient by inserting first inner track 124 of inner catheter 110 over the flexible guide wire and slowly advancing the deployment catheter 100 to the placement site. Tip balloon 152 may be partially inflated during insertion of deployment catheter 100 to dilate the vessel if necessary. Tip balloon 152 may then be advanced independent of push rod 112 and inflated to perform valvuloplasty on the existing valve by known methods. Microembolic filter tube 182 may also be employed prior to the valvuloplasty to capture any emboli during the procedure. If valve stent 20 is to be placed in the aorta, tip balloon 152 may be inflated in the aorta closer to the heart than the placement site to block blood flow during the placement procedure.

If valve stent 20 is to be placed at mitral valve 14, entry may be made through the right internal jugular vein. A guide wire is advanced through the entry site to the right atrium and interatrial septum 16. A catheter and needle combination (not shown) is advanced over the guide wire to interatrial septum 16 and used to puncture septum 16 and access left atrium 18. The guide wire is advanced into left atrium 18 and through mitral valve 14 and the catheter and needle combination is removed.

Deployment catheter 100 loaded with heparinized solution through side port means 116 is introduced by inserting first inner passage over the guide wire and slowly advancing deployment catheter 100 through the right atrium, interatrial septum 16 and into left atrium 18. Tip balloon 152 may be partially inflated in advance of deployment catheter 100 at the new passage in interatrial septum 16 to allow outer sheath 106 or microembolic filter 182 tube to pass through. Microembolic filter tube 182 may now be employed by advancing the proximal end of tube 182 until the filters flair. Tip balloon 152 is then placed within mitral valve 14 and valvuloplasty is performed by a known procedure.

From this point on, deployment of valve stent 20 is procedurally the same for all potential placement sites.

Figure 9A:
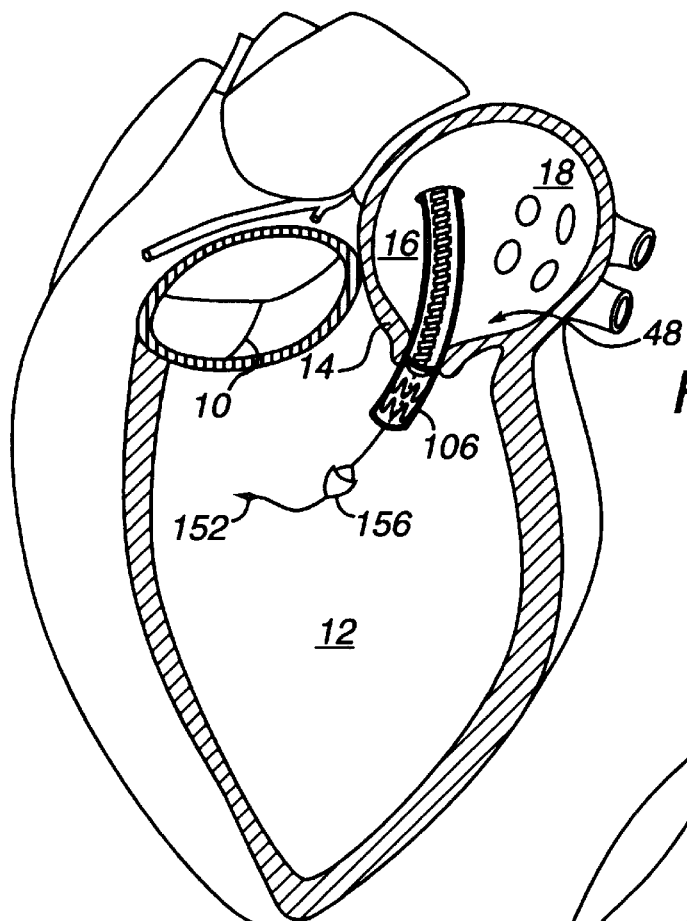

Contrast media may now be injected through first port means to the distal end opening of first inner track 124. Deployment catheter 100 is positioned so outer sheath 106 is extending through mitral valve 14 approximately one (1) centimeter as is seen in FIG. 9a. Deployment catheter 100 is rotated to match distensible fingers 46 to the structure of mitral valve 14 if necessary.

Figure 9B:
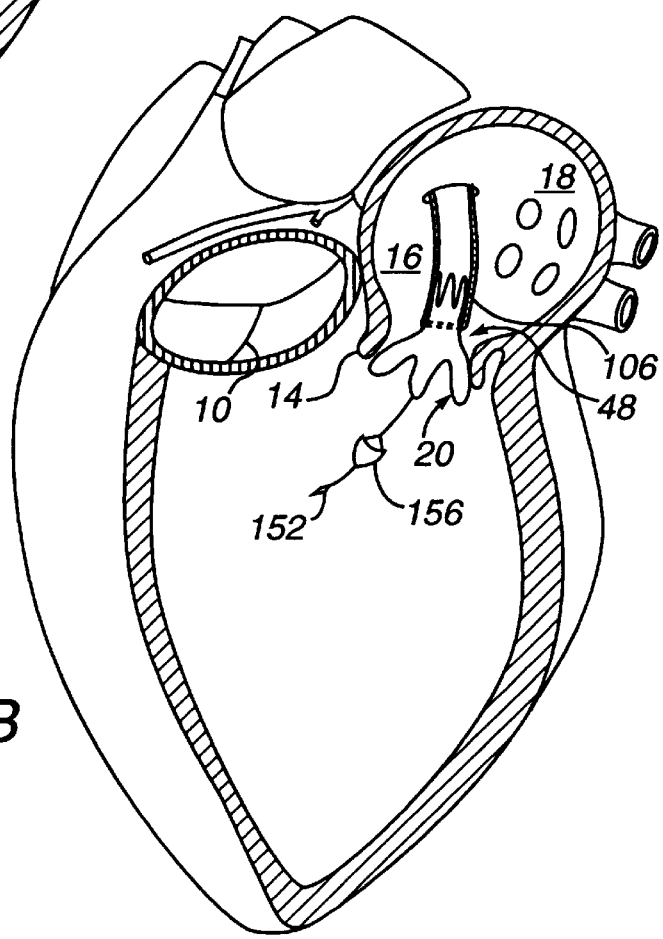

Deployment of the distal end of valve stent 20 is initiated by withdrawing outer sheath 106 approximately 11 to 13 mm while holding push rod 112 stationary. Distensible fingers 46 on the distal end of valve stent 20 will distend as the distal end is released from outer sheath 106 as is shown in FIG. 9b. While valve stent 20 is beginning to protrude from outer sheath 106, deployment catheter 100 may again be rotated and slightly advanced or withdrawn to optimize placement of valve stent 20. Inner catheter 110 is then moved to position expansion balloon 154 on the distal side of biological valve 22 yet within the distal end of valve stent 20 just deployed. The leaflets of biological valve 22 may be slightly overlapped by expansion balloon 154, but the base of biological valve must be free from contact with expansion balloon 154. Proper placement of valve stent 20 is verified by known means, including the introduction of additional contrast dye through the first inner port as described above. Expansion balloon 154 is then inflated to a pressure sufficient to hold the distal end of valve stent 20 secure against the living tissue as seen in FIG. 9c. This ensures proper placement is maintained during the remainder of the deployment procedure and allows valve stent 20 to mold itself quickly into the living tissue at the placement site and achieve a patent seal.

With expansion balloon 154 maintaining a friction fit against distal end of valve stent 20, outer sheath 106 is again withdrawn from valve stent 20 while maintaining the position of push rod 112. The proximal end of valve stent 20 is released once outer sheath 106 clears the proximal end of valve stent 20. Verification is once again performed, and if proper placement is attained, expansion balloon 154 is deflated as seen in FIG. 9d. Inner catheter 110 is withdrawn such that expansion balloon 154 is on the proximal side of the biological valve but within proximal end of valve stent 20 just deployed. Expansion balloon 154 may then be inflated again to seat the proximal end of valve stent 20 just deployed. Once more proper placement is verified.

Inner catheter 110 is now withdrawn such that it is clear of valve stent 20. If tip balloon 152 has been inflated to block blood flow during the procedure, it is deflated in small decremental steps to slowly increase blood pressure and flow downstream. This prevents damage to the downstream vessels and migration of valve stent 20 from sudden increased blood pressure. Valve stent 20 is now monitored for proper function and patency. The placement site is also monitored to ensure no damage has occurred to the living tissue. Tip balloon 152 or expansion balloon 154 may be advanced to either side of valve stent 20 and reinflated to further mold valve stent 20 to the living tissue if necessary. This should not be needed, however, because of the continuous outward force of super elastic stent 26.

If at any time it is necessary to retrieve valve stent 20 for repositioning or removal, the following procedure may be used. This procedure is applicable whether valve stent 20 is fully or partially deployed from outer sheath 106. First advance outer sheath 106 and push rod 112 to the proximal end of valve stent 20. Take up slack in suture loops 174 as outer sheath 106 is advanced by turning the spool handle in the appropriate direction. Take care not to extend the seal at the distal end of push rod 112 out of outer sheath 106. Next, while holding outer sheath 106 and push rod 112 stationary, turn the spool handle until distended fingers 46 of the proximal end of valve stent 20 are compressed to the diameter of outer sheath 106. Finally, again while holding push rod 112 stationary, advance outer sheath 106 over valve stent 20 and through the natural valve position until outer sheath 106 completely covers valve stent 20. Valve stent 20 may now be repositioned or removed. It may not be necessary to advance outer sheath 106 completely over valve stent 20 if repositioning is desired. In this case, advancing outer sheath 106 to collapse the distal end of valve stent 20 so that it is clear of living tissue may be sufficient. Either way, the procedure is simple and is harmless to valve stent 20.

Once properly placed, valve stent 20 function and leakage are verified, microembolic filter tube 182 is collapsed such that pocket filters 184 are flush against outer sheath 106, and suture loops 174 are cut and removed using optional blade 180 if provided. Then deployment catheter 100 is removed leaving the guide wire in place. A light emitting catheter capable of emitting light at the proper frequency to activate tissue bioadhesive 56 or packets 62 containing tissue bioadhesive 56 is inserted and energized. Bioadhesive 56 is exposed to the light sufficient to activate it and the light emitting catheter removed. An optical or other catheter may be inserted to verify any microleaks are closed or closing. Finally, any remaining catheters and the guide wire are removed and the entry site attended by standard procedure.

If necessary, prior to removing the guide wire and closing the entry site, a stapling device (not shown) may be introduced to secure valve stent 20 to the tissue. An alternative to staples is using the laproscopic suturing device (not shown) to percutaneously enter the vessel and place sutures around the sections of stent 26 if leaks occur after closing the entry site. Again, these are precautions which should not be necessary because of the superior sealing qualities of stent 26 which will maintain patency over the life of the patient. Also, either of these devices may be used to repair an internal puncture access if one was made.

What is claimed is:

1. A percutaneously implanted valve stent comprising:
    a tubular graft of bio-compatible material capable of conducting fluid, said graft capable of substantial deformation so as to conform to the interior surface of a patient's internal passage, said graft having proximal and distal ends;
    a radially compressible spring means for biasing said proximal and distal ends of said graft radially outward into dynamic conforming fixed engagement with said interior surface of said internal passage; and
    a valve means capable of blocking flow in one direction, said valve means being sealingly and permanently attached to the internal tubular portion of said graft or said spring means or both; wherein
    said graft material being attached to said spring means and enclosing said spring means.

2. The valve stent of claim 1, wherein said graft includes a middle portion extending between said proximal and distal ends, and said graft material is tapered to define a smaller fluid conducting area through said middle portion.

3. The valve stent of claim 1, wherein at least one of said tubular graft and said spring means contains a radio opaque marker.

4. The valve stent of claim 1, wherein said spring means is a wire spring comprising a pair of annular spring portions, and at least one connecting bar extending between said spring portions for connecting said pair of spring portions to one another.

5. The valve stent of claim 4, wherein each of said annular spring portions comprises a continuous zig-zag pattern of straight spokes connected by alternating crests and troughs, and said crest and troughs are of a predetermined radius.

6. The valve stent of claim 5, wherein said graft material is cut out between said crests of at least one of said pair of spring portions to define a plurality of radially distensible fingers.

7. The valve stent of claim 1, further including tissue adhesive means on the outside of said graft for bonding said graft to said interior surface of said passage and forming a substantially fluid-tight seal therebetween.

8. The valve stent of claim 7, wherein said tissue adhesive means comprises a plurality of packets including a degradable photo-sensitive outer packet material enclosing tissue adhesive, whereby said tissue adhesive may be released by exposing said packets to a light beam.

9. The stent of claim 7, wherein said tissue adhesive means is biocompatible and biodegradable.

10. The valve stent of claim 7, wherein said tissue adhesive remains adhesively inert until said adhesive is exposed to a light beam.

11. The valve stent of claim 7, wherein said tissue adhesive is at least one of fibrin glue, isobutyl 2 cyanoacrylate, and cryroparticipate.

12. The valve stent of claim 1, further comprising a deployment means for deploying said valve stent.

13. The valve stent of claim 1, further comprising a retreival means for retreiving said valve stent after deployment from said deployment means for removal from the patient.

14. The retreival means of claim 13, wherein said retreival means also allows repositioning of said valve stent within the patient.

15. The valve stent of claim 1, further comprising a filter means for capturing particles during deployment of said valve stent.

16. The valve stent of claim 1, wherein said graft material prevents contact between said spring means and living tissue.

17. A percutaneously implanted valve stent comprising:

a tubular graft of bio-compatible material capable of conducting fluid, said graft capable of substantial deformation so as to conform to the interior surface of a patient's internal passage, said graft having proximal and distal ends;

a radially compressible spring means for biasing said proximal and distal ends of said graft radially outward into dynamic conforming fixed engagement with said interior surface of said internal passage;

a valve means capable of blocking flow in one direction, said valve means being sealingly and permanently attached to the internal tubular portion of said graft or said spring means or both; and tissue adhesive means on the outside of said graft for bonding said graft to said interior surface of said passage and forming a substantially fluid-tight seal therebetween; wherein said graft material is attached to said spring means and encloses said spring means; and said tissue adhesive means is adhesively inert until said tissue adhesive means is exposed to light.

* * * * *

UNITED STATES PATENT AND TRADEMARK OFFICE
CERTIFICATE OF CORRECTION

PATENT NO. : 5,957,949

DATED : September 28, 1999

INVENTORS : Leonhardt et al.

It is certified that an error appears in the above-identified patent and that said Letters Patent is hereby corrected as shown below.

In column 3, line 48, the word "an" should be replaced by --a--.

In column 3, line 51, the word "an" should be replaced by --a--.

In column 4, line 19, the word "which" should be replaced by --with--.

In column 4, line 30, the phrase "is preferable" should be replaced with --are preferably--.

In column 7, line 62, the word "site" should be replaced by --site.--.

In column 8, lines 2-3, the word "preferable" should be replaced by --preferably--.

In column 8, line 25, the word "loosing" should be replaced by --losing--.

In column 8, line 50, the word "energize" should be replaced by --energized--.

In column 9, line 26, the word "uses" should be replaced by --used--.

*In the claims:*

In claim 9, column 12, line 63, the word "stent" should be replaces with --valve stent--.

In claim 10, column 12, lines 65-66, the phrase "tissue adhesive" should be replaced by --tissue adhesive means--.

UNITED STATES PATENT AND TRADEMARK OFFICE
CERTIFICATE OF CORRECTION

PATENT NO. : 5,957,949

DATED : September 28, 1999

INVENTORS : Leonhardt et al.

It is certified that an error appears in the above-identified patent and that said Letters Patent is hereby corrected as shown below.

In claim 11, column 13, lines 1-2, the phrase "tissue adhesive" should be replaced by -- tissue adhesive means--.

In claim 14, column 13, line 10, the phrase "retrieval means" should be replaced by -- valve stent--.

Signed and Sealed this

Twenty-ninth Day of May, 2001

Attest:

NICHOLAS P. GODICI

*Attesting Officer*   *Acting Director of the United States Patent and Trademark Office*